(12) United States Patent
Horey et al.

(10) Patent No.: US 6,581,391 B2
(45) Date of Patent: *Jun. 24, 2003

(54) ICE THICKNESS CONTROL SYSTEM AND SENSOR PROBE

(75) Inventors: Leonard I. Horey, Boca Raton, FL (US); Dennis W. Norwich, Sandy Hook, CT (US); Sam O. Sman, West Haven, CT (US); Mario G. Ceste, Wallingford, CT (US)

(73) Assignee: Technology Licensing Corporation, Tequesta, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/038,531

(22) Filed: Jan. 3, 2002

(65) Prior Publication Data

US 2002/0104322 A1 Aug. 8, 2002

Related U.S. Application Data

(60) Continuation-in-part of application No. 09/888,467, filed on Jun. 25, 2001, now Pat. No. 6,339,930, which is a division of application No. 09/561,881, filed on May 1, 2000.

(51) Int. Cl.[7] ............................................... F25C 1/00
(52) U.S. Cl. .......................................... 62/59; 62/138
(58) Field of Search ..................................... 62/59, 138

(56) References Cited

U.S. PATENT DOCUMENTS

| | | | | |
|---|---|---|---|---|
| 4,476,690 A | * | 10/1984 | Iannelli | 62/198 |
| 4,754,609 A | * | 7/1988 | Black | 62/200 |
| 4,823,556 A | | 4/1989 | Chesnut | 62/139 |
| 5,022,233 A | * | 6/1991 | Kirschner et al. | 62/138 |
| 5,056,320 A | * | 10/1991 | Winkler | 62/237 |
| 5,474,717 A | * | 12/1995 | Bucher et al. | 261/140.1 |
| 5,761,919 A | | 6/1998 | Wilson et al. | 62/138 |
| 5,761,920 A | | 6/1998 | Wilson et al. | 62/138 |
| 6,401,467 B1 | * | 6/2002 | Horey et al. | 62/138 |

OTHER PUBLICATIONS

Web Site Excerpt, Multiplex Company, Inc., "The Multiplex Remote Refrigeration Unit," Mar. 19, 2001, pp. 1–3.

* cited by examiner

Primary Examiner—William E. Tapolcai
(74) Attorney, Agent, or Firm—Pennie & Edmonds LLP

(57) ABSTRACT

The present invention provides an improved system and method for sensing the presence of ice, particularly applicable in the control of ice thickness in machines employing an ice bank such as a commercial beverage chiller. The chiller may be of the conventional type having a water bath with a cold element at least partially submerged therein. The cold element is cooled by a refrigerant such as freon to the point where ice forms and grows on the element, thereby forming an ice bank in the water bath. A temperature sensor, which preferably is a thermistor-type sensor comprising a bead disposed in a metal housing, is mounted on a carrier to allow the position of the sensor to be adjustable relative to the cold element. Circuitry is provided which is operative to detect the presence of ice by sensing a temperature signal from the temperature sensor and to control the thickness of the ice bank. A method of controlling the thickness of an ice bank is also disclosed. The invention has broad applicability to all types of machines wherein an ice bank is used.

24 Claims, 8 Drawing Sheets

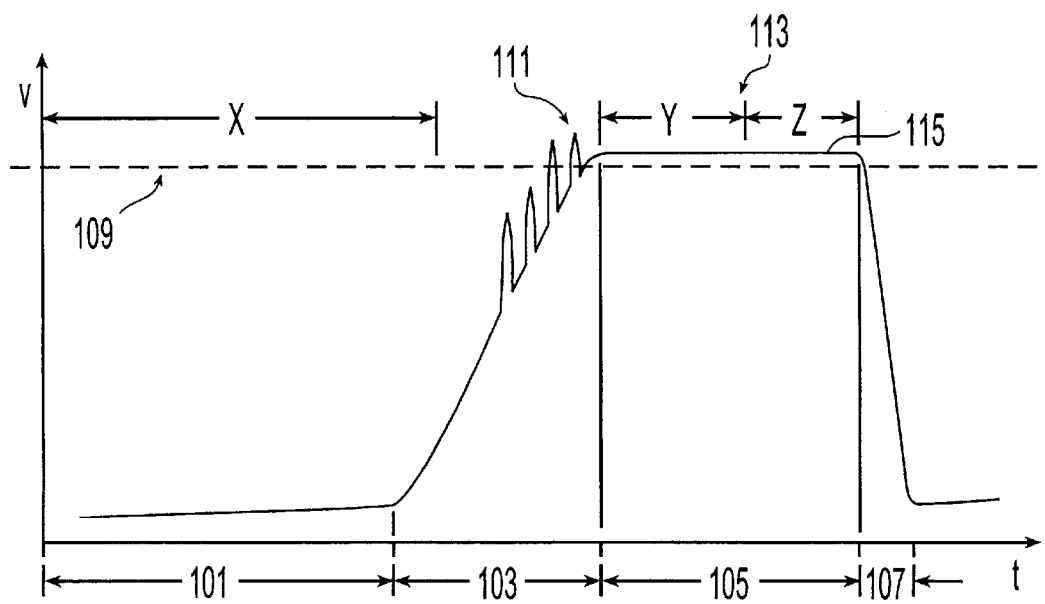
*Fig. 3*
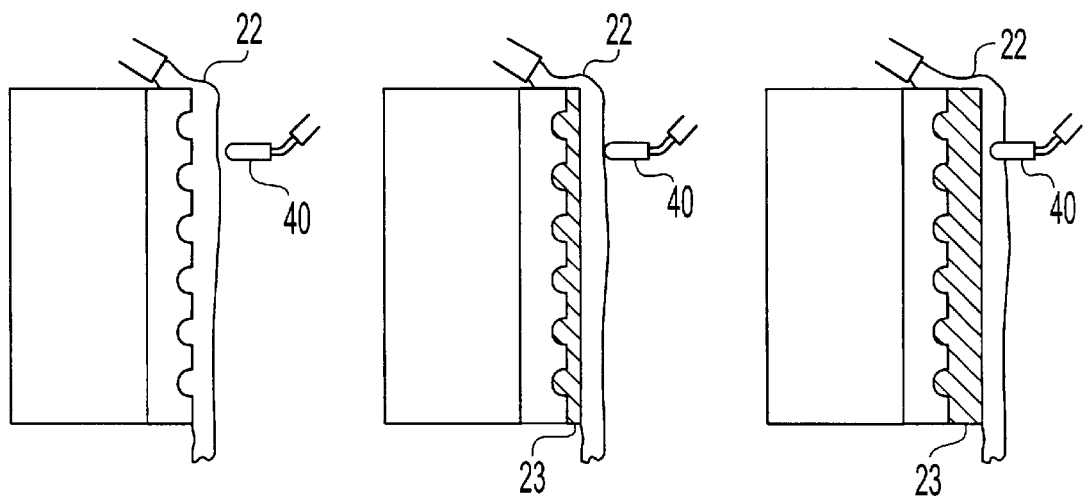
*Fig. 4a*　　　*Fig. 4b*　　　*Fig. 4c*

ICE THICKNESS CONTROL SYSTEM AND SENSOR PROBE

CROSS-REFERENCE TO RELATED APPLICATIONS

This is a continuation-in-part of U.S. patent application Ser. No. 09/888,467 filed Jun. 25, 2001, now U.S. Pat. No. 6,339,930 entitled "Ice Thickness Control System and Sensor Probe for Ice-Making Machines," which is division of U.S. patent application Ser. No. 09/561,881 filed May 1, 2000, entitled "Ice Thickness Control System and Sensor Probe for Ice-Making Machines," which are incorporated herein by reference.

TECHNICAL FIELD

The present invention relates to an improved ice thickness control system and associated sensor probe.

BACKGROUND OF THE INVENTION

Ice-making machines are known in the art. They can take various forms, but share the general basic attribute that water is brought into contact with a cold element, such as an ice plate or coil, which is cooled to below the freezing point of water. The cold element may be submerged in a pool of water, or the water may be provided in a flow over the cold element. In either design, ice will begin to form on the surface of the cold element, growing in size over time. Eventually, when enough ice is formed, it is "harvested," so that it may be used as cubes, etc.

For example, U.S. Pat. No. 5,761,919 discloses an automatic ice-making machine including a water reservoir 10 and a cold plate 14 with a surface shaped so as to form ice cubes. A pump 12 pumps the water from the reservoir over the cold plate. The cold plate is maintained at a temperature below freezing so that a thickness of ice 16 forms on the cold plate. A capacitance-sensing circuit 20 is used to determine when the built-up ice should be harvested.

It will be appreciated that all ice-making machines need a system, preferably an automated system, for determining when the ice has built up sufficiently to be harvested. It is important to be able to consistently harvest the ice at the right time, when the mass of ice being harvested has the appropriate thickness such that the resulting ice cubes will meet required dimensional tolerances. For example, if the ice is allowed to become too thick before harvesting, the ice cubes will tend to bind to each other, making them hard to separate. Alternatively, if the ice is harvested while it is still too thin, the ice cubes will be undersized, which is undesirable from the end user's perspective, as they will melt too quickly. Accordingly, there is a need in the art for an ice-making machine which can accurately determine when the ice should be harvested.

Typical prior art systems have used a variety of methods to detect the build-up of a sufficient amount of ice. Mechanical systems use micro-switches which are actuated when the ice surface contacts the switch. Such systems suffer from many drawbacks, including interference of ice with actuating parts, switch hysteresis, and tolerances.

Electrical resistance systems use metal a bridge sensor which conducts electricity when water is flowing over it. During the ice-making cycle, as the ice mass becomes thicker, it forces the flowing water to splash out further, eventually making continuous, or nearly continuous contact with the metal bridge, resulting in a substantially consistent signal in the associated circuit. This conductive signal is then interpreted by the system as an indication that the ice is thick enough to harvest. A serious drawback of this method is that water used in ice-making machines often contains impurities, which over time will coat a metal bridge sensor and stop it from conducting an electrical signal (the so-called "liming effect"). When this happens, the sensor must be serviced or replaced. In locations where there is a relatively high level of water impurities, this coating with impurities ("liming up") may occur very quickly. Accordingly, there is a need in the art for an ice-making machine ice sensor which is less susceptible to the liming problem than known sensors.

It is also known to use thermal detection systems which use temperature sensors placed appropriately such that when the ice builds out to and contacts the sensor, a unique thermal signature is presented to the detector. However, the prior art thermal detection systems have a poor signal-to-noise ratio, which makes them unable to provide reproducible harvesting cycles.

Accordingly, there is a need in the art for an ice-making machine sensor which has no moving parts, does not suffer from liming problems, and which can accurately and reproducibly determine when the ice should be harvested.

SUMMARY OF THE INVENTION

Accordingly, the invention addresses this need by providing an improved ice thickness sensing and control system using an improved temperature sensor and control logic having several adjustable delay times to optimize performance.

It will be appreciated by one of ordinary skill in the art that the control logic, including that implementing the delay times, may be implemented in hardware, firmware, software, or any combination of thereof, as a matter of design choice. Accordingly, the term "circuitry" as used herein means any combination of hardware, firmware, or software used to implement the control logic.

The invention is generally directed to an ice thickness control system which uses a temperature sensor mounted near the cold plate. As the ice thickens and gets closer to the sensor, the sensed temperature gets colder; finally when the ice is thick enough that it touches (or nearly touches) the sensor, the sensor will detect a very low temperature and will "notify" the control system to begin the harvesting process.

The invention is generally directed to a liquid-solidifying machine comprising a cold element, a liquid source, a temperature sensor, and circuitry associated with the sensor. The cold element includes a solid-forming surface which may be cooled to below the solidification point of the liquid. The liquid source provides liquid to the solid-forming surface such that a thickness of solid forms on the surface. The temperature sensor is provided with sufficient current that it self-heats to above the ambient temperature when the liquid-solidifying machine is in use. The circuitry associated with the sensor is operative to sense the temperature signal from the sensor, and detects when solid material formed on the cold surface is to be harvested.

In one embodiment, the liquid-solidifying machine is an ice-making machine; the liquid used in the system is water, and the solid is water ice. The temperature sensor in this embodiment self-heats sufficiently that no ice forms on the exterior surface of the sensor, preferably at least about 25° F. above ambient temperature when the machine is in use, more preferably at least about 75° F. above ambient temperature when the machine is in use. The temperature sensor is preferably a thermistor-type sensor, and may comprise a bead in a metal housing. The temperature signal from such sensors is not adversely affected by the deposition of impurities, from the liquid, on the exterior surface of the sensor. The temperature sensor may comprise a thermistor bead in a metal housing, the metal housing being mounted in a carrier, the position of the sensor relative to the solid-forming surface being adjustable.

The ice-making machine of the present invention comprises a cold element, a water source, a temperature sensor, and control logic associated with the sensor. The cold element includes an ice-forming surface which may be cooled to below the freezing point of water. The water source provides water to the ice-forming surface such that a thickness of ice forms on the surface during an ice-making cycle. The control logic detects when ice formed on the cold surface is to be harvested, and comprises a temperature signal threshold value, signal-sensing circuitry, threshold persistence circuitry, and harvesting cycle initiation circuitry. The temperature signal threshold value indicates when the thickness of ice is sufficiently close to the sensor such that it can be harvested. The signal-sensing circuitry is operative to sense the temperature signal from the sensor. The threshold persistence circuitry determines that the temperature signal has consistently remained above the threshold value for a threshold persistence time duration since the temperature signal first exceeded the threshold value. The harvesting cycle initiation circuitry initiates a harvesting cycle, during which the ice is removed from the ice-making surface.

The control logic may further comprise circuitry for determining that, starting from the beginning of the ice-making cycle, a minimum harvest time duration has elapsed, before the harvesting cycle can be initiated. It may also further comprise circuitry for determining that, starting from the end of the threshold persistence time duration, a harvesting delay time duration has elapsed, before a harvesting cycle can be initiated. The control logic may further comprise circuitry for determining that, starting from the end of the harvesting cycle, a recycling delay time duration has elapsed, before another ice-making cycle can be initiated.

A method of operating an ice-making machine is also provided, comprising the steps of: (a) providing a cold element; (b) providing a water source; (c) providing a temperature sensor; (d) providing circuitry associated with the sensor; (e) providing the circuitry with a temperature signal threshold value (which indicates when the thickness of ice is sufficiently close to the sensor such that it can be harvested); (f) initiating an ice-making cycle (during which the ice-making surface is cooled to below the freezing point of water, and water is provided to the ice-forming surface such that a thickness of ice forms on the surface); (g) a threshold persistence determination step, in which it is determined whether the temperature signal has consistently remained above the threshold value for a threshold persistence time duration since the temperature signal first exceeded the threshold value; and (h) a harvesting cycle initiation step, during which the ice is removed from the ice-making surface. The cold element includes an ice-forming surface which may be cooled to below the freezing point of water. The water source can provide water to the ice-forming surface. The circuitry associated with the sensor detects when ice formed on the cold surface is to be harvested, said circuitry being operative to sense the temperature signal from the sensor.

The steps (f) through (h) may be performed in alphabetical order, and may be repeated more than once. The method may include the further step of determining that, starting from the beginning of the ice-making cycle, a minimum harvest time duration has elapsed, before a harvesting cycle can be initiated. The method may also include the further step of determining that, starting from the end of the threshold persistence time duration, a harvesting delay time duration has elapsed, before a harvesting cycle can be initiated. The method may also include the further step of determining that, starting from the end of the harvesting cycle, a recycling delay time duration has elapsed, before another ice-making cycle can be initiated.

The ice thickness control system of the invention also has broad applicability to machines in which the cold element is submerged in a pool of water or water bath as mentioned above. Such machines may employ an ice bank formed by the submerged cold element to serve numerous commercial purposes.

In one embodiment, a machine for forming an ice bank comprises a cold element having at least one ice-forming surface that is cooled to below the freezing point of water. At least part of the cold element is submerged in a pool of water which is contained by a tank such that an ice bank forms and grows around the surface. In one embodiment, the cold element is comprised of refrigerant-cooled coils configured to form an ice bank. However, the cold element may be configured to have any suitable geometric configuration (e.g., plate, combination plate and coils, etc.) that is capable of being cooled by a refrigerant to form an ice bank.

At least one temperature sensor is included which is located inside the tank and positioned so that it may be contacted by the ice bank as it forms and grows. Circuitry associated with the sensor is provided for detecting when the ice bank reaches the sensor such that the ice bank touches or nearly touches the sensor. The circuitry is operative to sense a temperature signal from the sensor, and thereby may be used to control the growth of the ice bank.

In one embodiment, the temperature sensor may be sufficiently self-heated to prevent ice from forming on the sensor which could cause a false indication that the ice bank has reached the sensor, when in reality it has not. Preferably, the sensor is provided with sufficient electric current to create the self-heating.

The temperature sensor is preferably a thermistor-type sensor which in one embodiment comprises a bead in a metal housing. The thermistor-type sensor is preferably of the self-heated design.

In another embodiment, a second temperature sensor is provided in addition to the first sensor, and the circuitry is further operative to sense a temperature signal from the second sensor. The first sensor and the second sensor are spaced apart axially by a predetermined distance along the direction of the growth of the ice bank such that the sensors may be used to control the growth of the ice bank. In one embodiment, the two sensors may be contained in a single probe housing. In another embodiment, however, the two sensors may be contained in separate housings for each sensor. Both sensors may be self-heated to prevent ice from forming on either sensor.

In one embodiment, the ice bank machine utilizing the ice thickness control system of the present invention may be a beverage chiller. A beverage chiller includes an exterior casing in which a tank containing water is disposed. A refrigerant compressor associated with the beverage chiller is provided, which may or may not be contained within the casing of the chiller. A plurality of coils at least partially submerged in the water is included that are connected to the compressor to form a closed flow loop in which a commercially-available refrigerant is circulated; whereby, the coils are cooled to below the freezing point of water to form an ice bank around the coils.

The chiller includes a temperature sensor that is located and positioned inside the water tank such that it may be touched or nearly touched by the ice bank as it grows. Circuitry associated with the sensor is provided for detecting when the ice bank reaches the sensor; the circuitry being operative to sense a temperature signal from the sensor. The circuitry controls the growth of the ice bank. In one embodiment, the circuitry controls the growth of the ice bank by turning off the compressor when the ice bank reaches the temperature sensor.

In one embodiment, the temperature sensor of the beverage chiller is a thermistor-type sensor comprising a bead in a metal probe housing. In another embodiment, the sensor is sufficiently self-heated to prevent ice from forming on the sensor.

The beverage chiller in another embodiment may further comprise a second sensor in addition to the first sensor, with the circuitry being further operative to sense a temperature signal from the second sensor. Both temperature sensors are spaced apart axially by a predetermined distance along the direction of the growth of the ice bank. In one embodiment, the circuitry turns on the compressor when the ice bank recedes from the second sensor such that it no longer touches or nearly touches the second sensor. In one embodiment, the two temperature sensors are contained in a single probe housing.

In one embodiment, the beverage chiller further includes a plurality of beverage syrup cooling coils that are at least partially submerged in the water tank.

A method of operating a machine for forming an ice bank is provided, comprising the steps of:
  a. providing a tank having water disposed therein;
  b. providing a cold element including at least one ice-forming surface, at least part of the cold element being submerged in the water such that an ice bank can form and grow around the surface;
  c. providing at least a first temperature sensor;
  d. providing circuitry associated with the sensor for detecting when ice reaches the sensor, the circuitry being operative to sense a temperature from the at least first sensor;
  e. cooling the cold element to below the freezing point of water;
  f. forming and growing an ice bank around the ice-forming surfaces;
  g. sensing a temperature signal from the sensor;
  h. determining when the temperature signal reaches a predetermined threshold value; and
  i. controlling the operation of the machine to control the growth of the ice bank.

In one embodiment, the sensor used in the method of operating an ice bank-forming machine is a thermistor-type sensor that is sufficiently self-heated to prevent ice from forming on the sensor. In another embodiment, the method of operating the ice-bank forming machine includes turning the machine off to stop the growth of the ice bank when the temperature threshold value is reached. The method may further comprise providing the circuitry with a predetermined time delay to turn the machine back on to restart the growth of the ice bank when the time delay has been met.

The method of operating an ice-bank forming machine may further comprise the step of providing a second temperature sensor, making the circuitry operative to sense a temperature signal from the second sensor, and determining when the temperature signal from the second sensor reaches a predetermined second threshold value. In one embodiment, the method further comprises turning the machine on to restart the growth of the ice bank when the temperature signal from the second sensor reaches the predetermined second threshold value.

BRIEF DESCRIPTION OF THE DRAWINGS

The features and advantages of the present invention will become more readily apparent from the following detailed description of the invention in which like elements are labeled similarly and in which:

FIG. 3 illustrates the temperature signals present in the temperature-detection circuitry of FIG. 1;

FIGS. 4A–4C are schematic views of the ice-making machine of the present invention, with various amounts of ice formation, corresponding to various temperature signals depicted in FIG. 3;

DETAILED DESCRIPTION OF THE PREFERRED EMBODIMENTS

Figure 1:
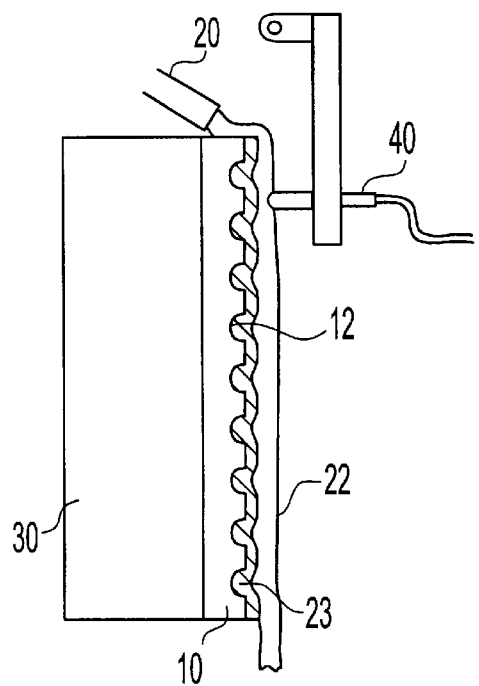
FIG. 1 is a schematic view of the ice-making machine of the present invention, including a temperature sensor and temperature-detection circuitry.

Referring to FIG. 1, an ice-making machine is schematically depicted as including a vertical cold plate 10, a water source 20, and a refrigeration system 30. It can be seen that the surface 12 of the cold plate on which the ice forms may be shaped with ridges and valleys so as to provide discrete cubes of ice when the ice is harvested. In this shaping aspect, the cold plate may be analogized to a vertically oriented ice cube tray as found in standard home refrigerators.

In operation, water 22 from source 20 flows over the ice-forming surface 12. Due to the refrigeration cooling the plate, the water turns to ice 23, progressively building up in thickness, as measured from surface 12, over time. When the system determines that the ice is fully formed, it is harvested.

The harvesting may be accomplished using a valve system, for example, such that instead of cold liquified gas being pumped past the cold plate to cool it, the exhaust or hot gas from the cooling compressor can be pumped past the cold plate, warming the plate and causing the ice to fall away. The completion of the harvesting step can be determined by known methods, either implicitly (determining that the harvesting has succeeded a given period of time after the cold plate was warmed up), or by a direct physical harvested-ice sensor, such as a mechanical flap switch which senses when the ice cubes drop away from the plate.

Figure 2:
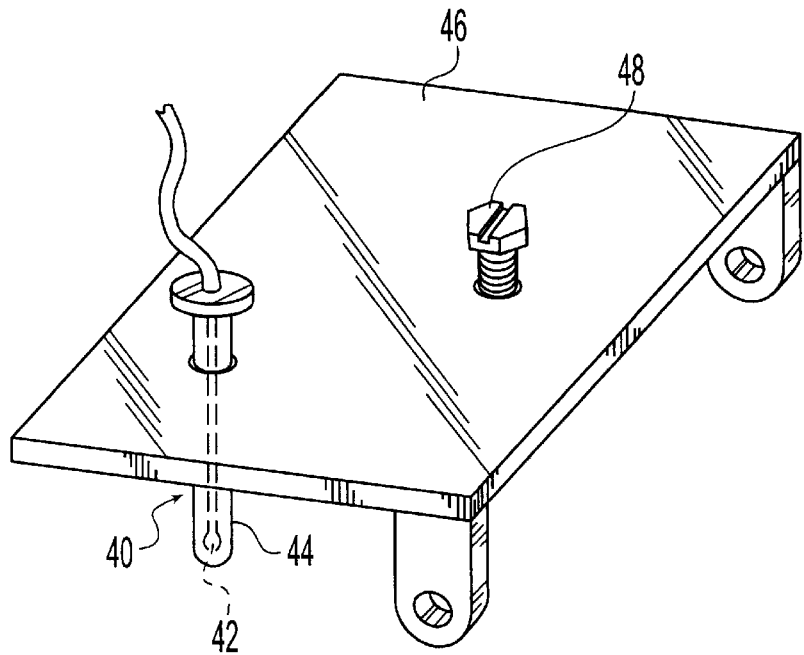
FIG. 2 is a schematic view of a temperature sensor.

The thermistor probe temperature sensor 40 is depicted in FIG. 2. In order to achieve accuracy and repeatability in the determination of the appropriate harvest time, a self-heated thermistor bead 42 is encapsulated in a metal housing 44, which is then in turn mounted in a carrier 46. The housing may be a thin-walled food-grade metallic well, such as a nickel-plated eyelet, in which the thermistor bead can be housed with the bead touching the extreme interior wall of the eyelet. The eyelet may then be inserted into the carrier and sealed. The carrier may be a molded plastic part and may further be provided with a set screw 48 to allow adjustment of the separation between the sensor and the ice-forming surface, in order to allow for adjustment of the harvested ice thickness, and to ensure that the sensor is positioned at the same separation from the ice-forming surface 12 at the beginning of each ice-making cycle. The sensor is preferably of low mass, designed so that it has maximum physical protection while still having the minimal practicable thermal mass.

As seen in FIG. 2, the sensor is preferably positioned near an area of minimum ice thickness (i.e., near a "ridge" on the cold plate). This insures that at such time as the ice is sufficiently thick to be harvested, the sensor has not become embedded in, or surrounded by, the ice, as would occur if it was positioned near an area of maximum ice thickness (i.e., near a "valley" on the cold plate).

Referring to FIG. 3, a graph of a signal in the temperature sensing circuit versus time is depicted. The graph shows the "temperature signal" which is physically the voltage signal from the thermistor probe. In typical circuits, such as shown here, the voltage signal is inversely proportional to the actual sensed temperature.

During the initial portion 101 of the ice-making cycle, the sensor 40 is sensing a steady-state temperature. This corresponds to the situation depicted in FIG. 4A, in which there is little or no ice formation, such that the ice mass 23 is a substantial distance from the sensor 40. In this regard, the self-heating feature of the sensor is significant, because the current in the thermistor is sufficient to heat it through the resistive heating effect, and thus the temperature of the sensor is internally biased. Depending on the level of current supplied and the physical characteristics of the thermistor, the self-heating effect may be substantial, biasing the temperature of the sensor above any possible ambient air temperature which would be expected during the normal operation of the ice-making machine, for example to 150° F.

When exposed only to the air, the temperature sensed by the sensor will stabilize at its self-heated temperature. As the approaching ice mass forces the water curtain over the sensor, the sensed temperature will drop down, and eventually, when a sufficient amount of the water curtain covers the sensor, the sensed temperature will drop below the threshold temperature. For consistency with usage in the art, the condition when the sensed temperature drops below the threshold value which indicates that the ice is ready to harvest may be referred to as the temperature threshold being "exceeded."

The thermistor-type sensor is advantageous because it does not operate based on conductivity, and thus the signal from the thermistor-type sensor is not adversely affected even when it becomes coated water or deposits from the water.

The voltage value will remain substantially constant at the low steady state value, while the ice thickness 23 begins to build up on the plate (but while it is still substantially far away from the sensor). As the water begins to get closer to the sensor however (portion 103 of the ice-making cycle, and as depicted in FIG. 4B), the sensed temperature will begin to decrease, with a resulting increase in the voltage. Ultimately as the water actually comes into contact with and envelops the sensor (portion 105 of the ice-making cycle, and as depicted in FIG. 4C), the sensed temperature will reach a minimum steady state value, and the voltage will correspondingly reach a high steady state value, which will persist until the harvesting process is performed, at which time the ice will fall away from the plate and the sensor, again exposing the sensor to the ambient temperature, thus increasing its temperature (portion 107 of the ice-making cycle). Following the harvesting, the system can be configured to automatically begin another ice-making cycle. The system may include a recycling delay time duration between the end of the harvesting cycle and the start of the subsequent ice-making cycle.

In general terms, the ice is ready for harvesting when the voltage exceeds a temperature signal threshold value 109 corresponding to the low steady state temperature of the sensor when the ice gets sufficiently close to the sensor. As a practical matter, the harvesting threshold voltage value should be set slightly below the maximum voltage which is produced by the sensor when it is fully enveloped in ice.

Based on practical considerations as determined by research and experimentation, there are three different delays, or time durations, which may be provided in the system:

The first delay or time duration is the Minimum harvest time delay (X). The temperature sensed by the thermistor is essentially ignored for a time X starting from the beginning of the ice-making cycle. This serves as a "reasonableness test," reflecting the fact that basic physical laws dictate that the ice cannot possibly be ready to harvest until a certain minimum amount of time has elapsed in the cycle, regardless of what the sensor indicates.

In the example of FIG. 3, it can be seen that temperature signal does not reach the threshold until after the delay X has expired. In a properly operating system, this would generally be the case.

The second delay or time duration is the Threshold persistence (Y). During the intermediate part 103 of the ice-making cycle, the temperature signal from the thermistor will not provide a consistently smooth or consistent value but rather exhibits fluctuations, seen as the "jaggies" in the graph of FIG. 3. The jaggies in the signal are particularly a problem as the ice surface gets close to the thermistor, since the running water flowing on the outer surface of the ice will tend to splash; the splashing droplets of water hitting the thermistor will cause the thermistor to momentarily sense a low temperature although it is not actually appropriate yet to perform the harvest. Thus this delay or duration Y may be implemented to require that the signal persists above the harvest threshold value for a certain amount of time (referenced to when the threshold is first exceeded), before harvesting may begin. If the threshold is only exceeded momentarily, and the signal dips back below the threshold before time Y has elapsed (as occurs at 111 in FIG. 3), harvesting will not begin. But when the signal exceeds the threshold and stays above the threshold for at least delay Y (as at 113), harvesting may begin, as long as other conditions (for example, the minimum harvest time delay) allow it.

The third delay or time duration is the Harvesting delay (Z); this is an optional delay or duration which may quite possibly be set to zero. It is adjusted based on the ambient temperature of the ice sensor, and is provided give the option of making sure the ice is sufficiently fully formed or "cured." This delay Z is referenced to the end of the delay Y, and is graphically reflected as the right-hand portion of the flat "plateau" region 115 of the graph of FIG. 3.

Figure 5:
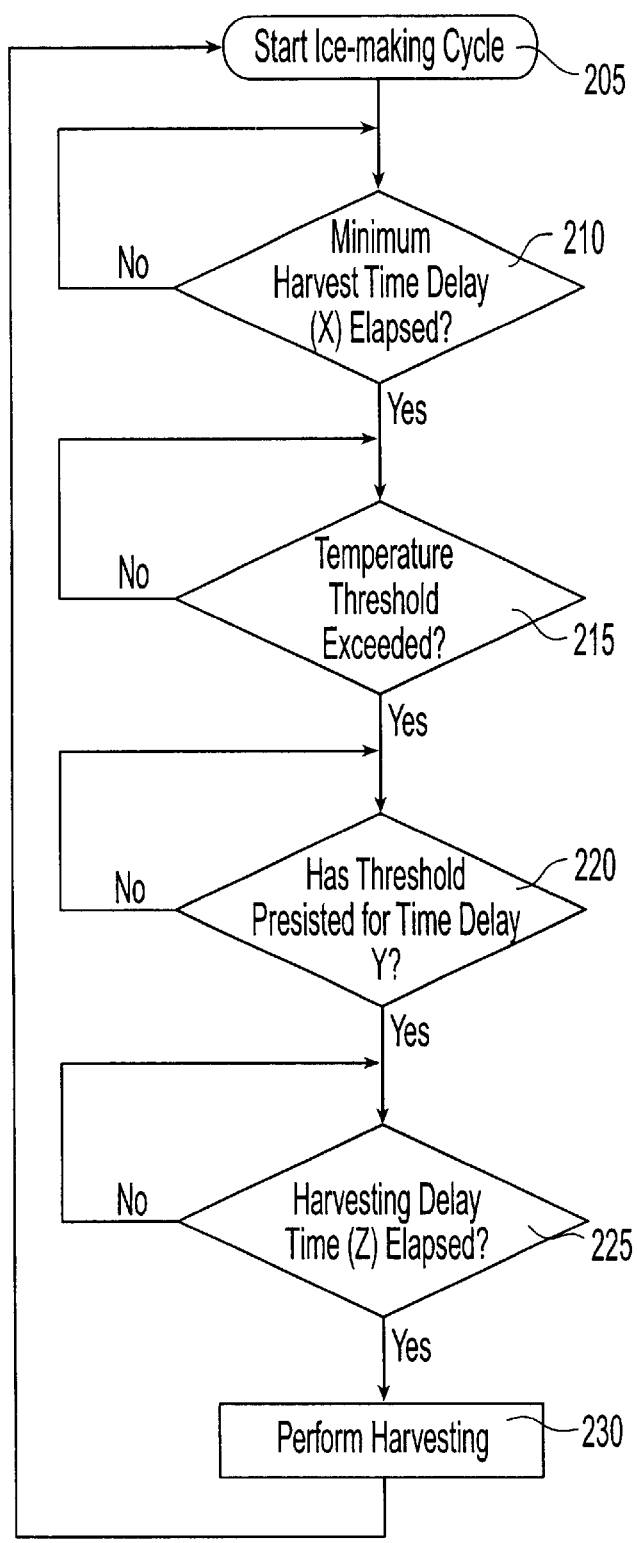
FIG. 5 is a flowchart describing an exemplary logic flow of the present invention.

FIG. 5 illustrates a logic flow chart for one implementation of the logic using the delay times discussed above. The logic process 200 begins the ice-making cycle in step 205. A test is performed in step 210 to determine whether the minimum harvest time delay (X) has elapsed, to serve as a "sanity check" in the logic, to ensure that harvesting cannot begin before the ice can reasonably be expected to be ready to harvest. Processing does not proceed to step 215 until step 210 determines that the minimum harvest time delay has elapsed. In step 215, a test is performed to determine whether the temperature threshold has been exceeded, indicating that the ice mass may have built up sufficiently to be ready to harvest. Processing does not proceed to step 220 until step 215 determines that the temperature threshold has been exceeded. In step 220, a test is performed to determine whether the temperature has persisted beyond the threshold for threshold persistence time delay (Y), to ensure that the temperature sensed in step 215 was not a transient spike, such as that caused by a splash of cold water. In the illustrated embodiment, if the persistence delay has not been satisfied, the logic simply stays in a loop at step 220 until it is satisfied. In an alternate embodiment however, the logic for the "NO" output of step 220 may return control to above step 215, such that processing does not return to step 220 until the test of 215 is satisfied. When it is determined that the persistence delay has been satisfied, processing proceeds to step 225, where a test is performed to determine whether the harvesting delay (Z) has elapsed. Processing does not proceed to the harvesting step 230 until that delay has elapsed. When processing has proceeded to step 230, and the harvesting has been performed, processing returns to step 205, where a new ice-making cycle is initiated.

The present invention is discussed herein with reference to a preferred embodiment using a ice plate, but one of ordinary skill in the art will readily understand that the invention is not limited to ice plate systems, but rather finds general application for use with any ice-making system such as those employing ice banks or ice packs. Indeed, the system is not limited to ice-making machines, but may generally be used in any application in which it is desired to detect the formation of ice. It will be further be appreciated that although the present invention is discussed in an embodiment of an ice-making machine, the invention is more generally applicable to any system in which any material (not only water) in its liquid state is cooled to its solid state. The modifications appropriate for such other applications may readily be realized by those of ordinary skill in the art and who have been equipped with the understanding of the structure and operation of the present invention as set forth in the above description. It will also be appreciated by one of ordinary skill in the art that the thermistor bead temperature sensor disclosed herein may be used whether or not the delay times are incorporated into the control system, and vice versa. Finally, it will be appreciated by one of ordinary skill in the art that the details of the design of the temperature sensor thermistor, the sensing circuitry, and the related software is a routine matter of design choice, and that the invention is not limited to the particular embodiments of those features depicted herein.

Figure 6:
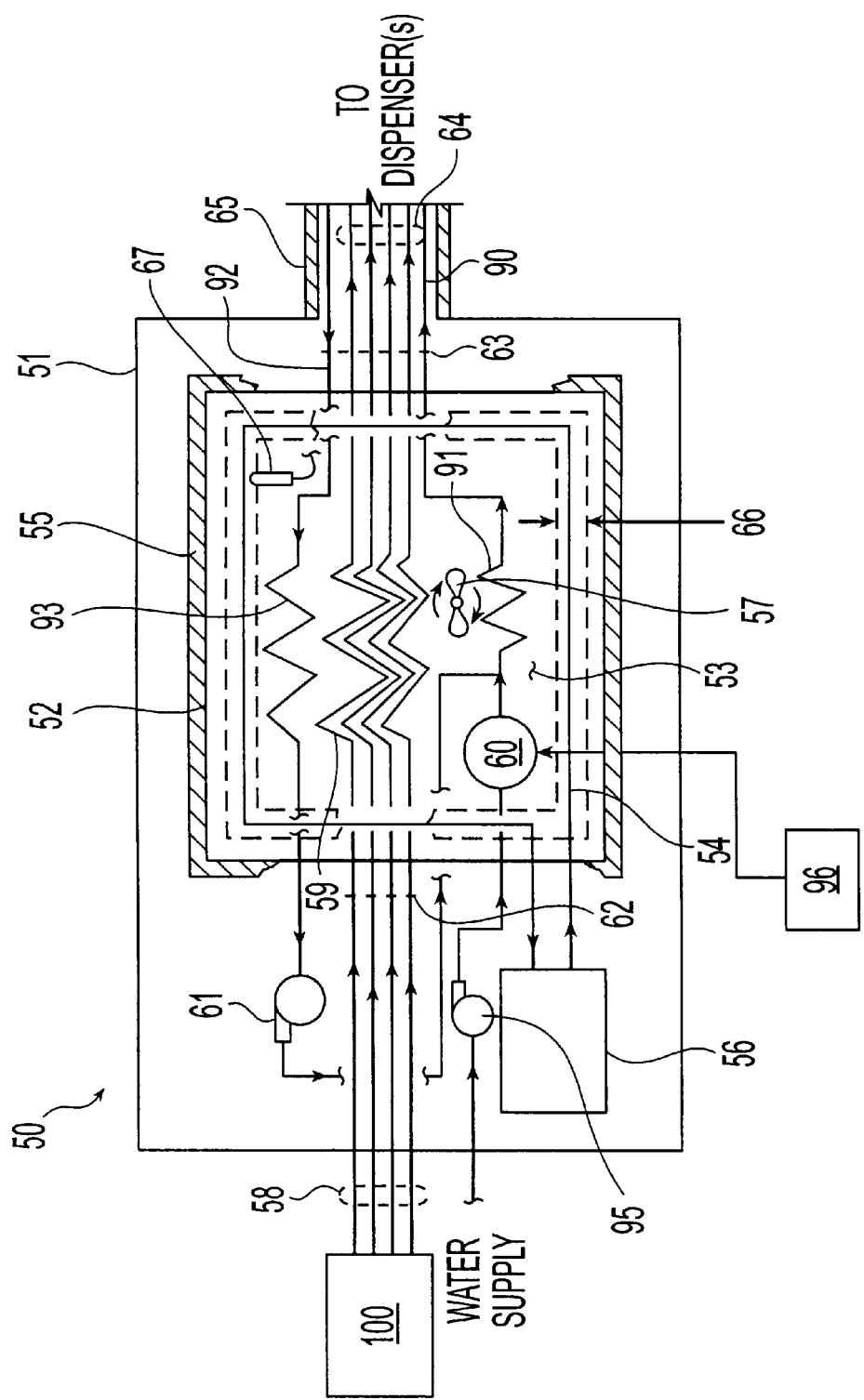
FIG. 6 is a schematic view of a beverage chiller of the present invention including a temperature sensor and temperature-detection circuitry.

FIG. 6 schematically depicts one example of a machine that employs an ice bank to which the present invention may be applied. The machine shown is a beverage chiller, which is essentially a refrigeration machine, that is used in the food service industry to chill beverages such as soda, juice, beer, wine, etc. before they are dispensed and served from a beverage dispensing unit. Such chillers are commonly used to chill soft drink syrup and carbonated water before they are combined and mixed in a beverage dispensing unit to produce carbonated soft drinks. Beverage chillers may be an integral part of the dispensing unit, or they may be separate machines that are placed near to or remote from the dispensing unit.

Referring to FIG. 6, the beverage chiller 50 generally comprises an exterior casing 51, typically made of metal, which contains various components. A leak-tight water tank 52, which is located inside the casing, holds a very cold water bath 53. A layer of insulation 55 preferably surrounds the tank 52 to reduce heat transfer to/from the ambient environment, to assist in keeping the water cold. The tank 52 may be made of metal (i.e., stainless steel, enameled steel, aluminum, etc.), plastic, or any other suitable material as is commonly used in the art.

A cold element is provided which preferably comprises water bath cooling coils 54 that encircle the inside of the water tank 52. The coils 54 are preferably made of copper, but may be made of any other metal having suitable heat transfer properties for the intended application. The cooling coils 54 are connected to a refrigerant compressor 56 in a manner which creates a closed flow loop in which a commercially available conventional refrigerant (e.g., freon) may circulate. The circulating refrigerant absorbs heat in the tank to chill the water bath 53 to a point which freezes the water around the coils, thereby forming and growing an ice bank 66 which keeps the water bath at an ice cold temperature. Depending on the geometric configuration of the cooling coils 54 and the water tank 52, the ice bank 66 may generally grow to approximate the shape of a large block of ice that surrounds the coils and extends around the inside perimeter of the water tank along the sides, and from top to bottom.

Preferably, the compressor 56 is located inside exterior casing 51 of the chiller 50. It should be noted, however, that the compressor 56 may be physically located outside the casing 51 and fluidly connected to the water bath cooling coils 54 via external refrigerant tubing lines (made of, e.g., copper) through which the refrigerant can flow to and from the coils. In this latter case of a physically separate compressor 56, it is preferable to locate the compressor as close to the chiller 50 as possible to reduce heat loss to the ambient environment through the connecting refrigerant tubing lines as much as practicable. Preferably, the external refrigerant coolant lines are insulated.

A temperature probe sensor 67, preferably a thermistor-type sensor, monitors and controls the thickness of the ice bank 66 that is formed in conjunction with circuitry associated with the probe. An electric motor-driven agitator 57 may also be provided in the water tank 52 to keep the water bath 53 agitated and at a fairly uniform temperature throughout the tank. Thus, the agitator also helps keep the ice bank 66 at a substantially uniform thickness throughout the water tank 52.

Beverage conveying tubing which in this embodiment is syrup conveying tubing 58 delivers warm syrup to the beverage chiller 50 from a syrup containers which may comprise a variety of individual syrup storage vessels of differing flavors. The syrup conveying tubing 58 is fluidly connected to syrup cooling coils 59 having inlet ends 62. Typically, a plurality of individual syrup conveying tubing and cooling coils 58, 59 are provided depending on the number and types of beverages to be served. The syrup cooling coils 59 are configured to provide multiple passes within the cold water bath 53 (better seen in FIGS. 7 and 8), thereby maximizing heat transfer between the bath and coils 59. When the syrup leaves the beverage chiller, it has been cooled to a very low temperature by the water bath 53. The syrup cooling coils 59 have outlet ends 63 which are connected to syrup delivery tubing 64 that transfers the cooled syrup to a beverage dispenser(s) (not shown). The syrup delivery tubing 64 preferably is routed to the dispenser (s) in an insulated conduit 65 to maintain the syrup at an ice cold temperature.

If carbonated beverages are to be made and served, the beverage chiller 50 may also contain a carbonator tank 60 to which filtered water and carbon dioxide are supplied and mixed therein. In one embodiment, a filtered water pump 95 may be provided as an integral part of the chiller 50 to pump room temperature filtered water to the carbonator tank 60, wherein the water is chilled to a very cold temperature. The filtered water supply may be from a municipal water source, well source, etc. which is run through any commercially available water filtration equipment. Alternatively, unfiltered water may also be used. Carbon dioxide is provided to the carbonator tank 60 via piping or tubing from on-site storage tanks 96.

At least part of the carbonator tank 60 is submerged in the cold water bath 53 to produce the cold carbonated water. Cold carbonated water flows from the carbonator tank 60, through carbonated water cooling coils 91 connected to the tank which preferably may be provided to further cool the carbonated water, and then through carbonated water delivery tubing 90 to the beverage dispenser(s). The delivery tubing 90 is preferably routed in the same insulated conduit 65 as the syrup delivery tubing 64. The carbonated water cooling coils 91 are submerged in the water bath 53 (similarly to the syrup cooling coils 59) to cool the carbonated water as it flows through the cold water bath 53 to the dispenser(s). Any number of carbonated water cooling coils 91 and delivery tubing 90 lines may be used depending on the number of beverage dispensers to be supplied with cold carbonated water.

As shown in FIG. 6, a flow recirculation loop may further be provided to continuously recirculate cold carbonated water between the dispenser(s) and beverage chiller 50. The carbonated water recirculation loop is made by additionally providing carbonated water return tubing 92 and a recirculation pump 61 which provides the motive force for the recirculation flow. Preferably, additional carbonated water cooling coils 93 that are connected between the return tubing 92 and the carbonated water recirculation pump 61 may further be provided. The carbonated water recirculation flow loop further ensures that cold carbonated water is continuously available at the dispenser(s), and also helps keep the syrup cold in route to the beverage dispensers.

In operation, warm beverage syrup flows from syrup storage containers or vessels (not shown) through the syrup conveying tubing 58 to the chiller 50. The syrup then travels through the syrup cooling coils 59 which are immersed in the ice cold water bath 53 as described above to reduce the syrup's temperature the desired amount (e.g., typically, but not limited to, about 40 degrees Fahrenheit). The syrup then flows on to the beverage dispenser(s) where it is mixed with cold carbonated water which may also be cooled by the beverage chiller as previously described.

Although the beverage chiller has been described with reference to FIG. 6 using an embodiment wherein raw ingredients for the final beverage are chilled (i.e., syrup and carbonated water), the chiller may be used simply to chill a beverage which requires no further processing or combination with other ingredients to produce the final beverage (e.g., beer, wine, juice, etc.). Accordingly, the invention is expressly not limited to chillers used for carbonated beverages and has broad applicability to chilling many types of beverages or food products used in a liquid form where it is desirable to cool them as will be apparent to those in the food service industry.

Figure 7:
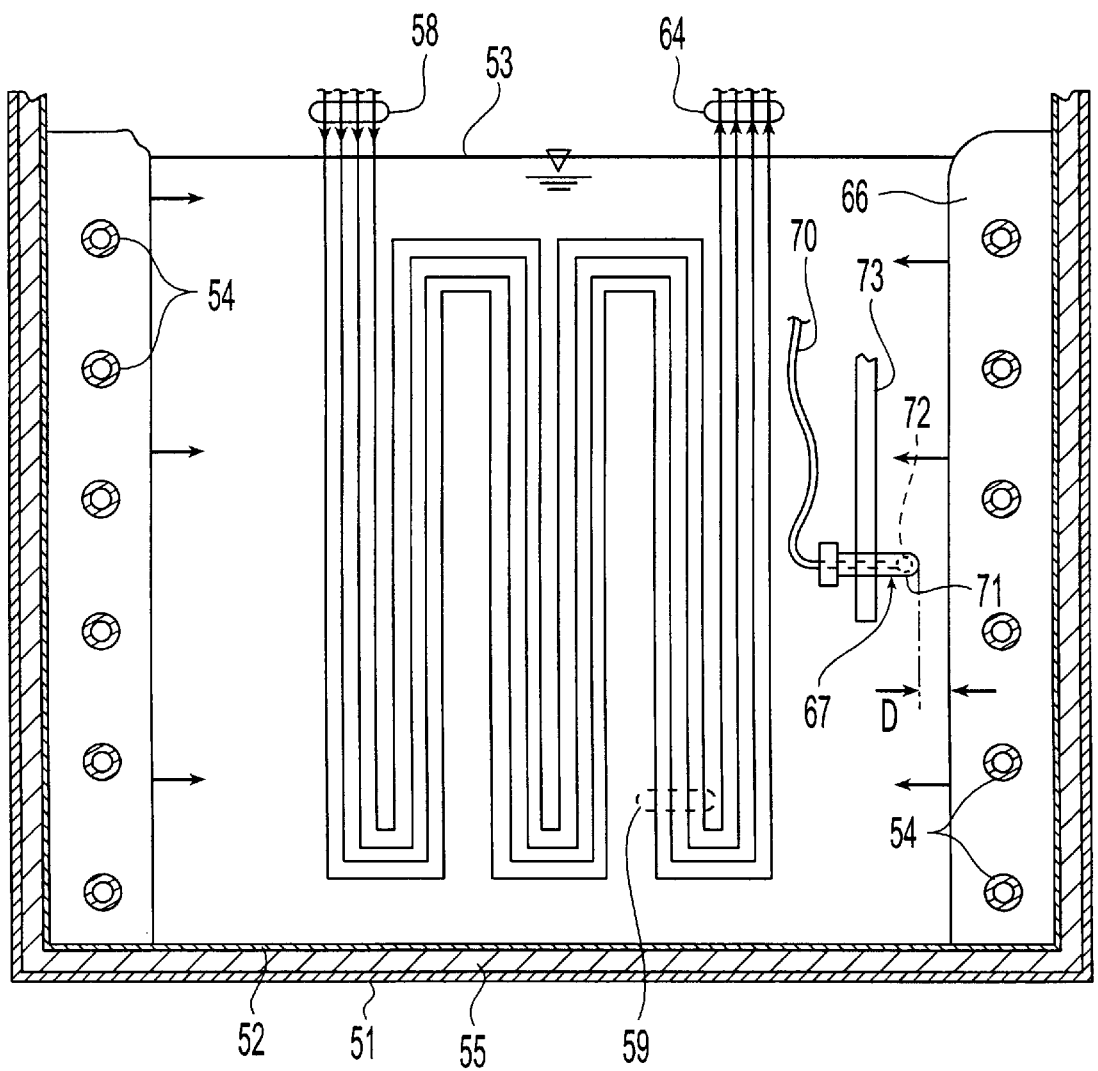
FIGS. 7 & 8 are schematic cross-sectional side views of a beverage chiller of the present invention including a temperature sensor and temperature-detection circuitry.
Figure 8:
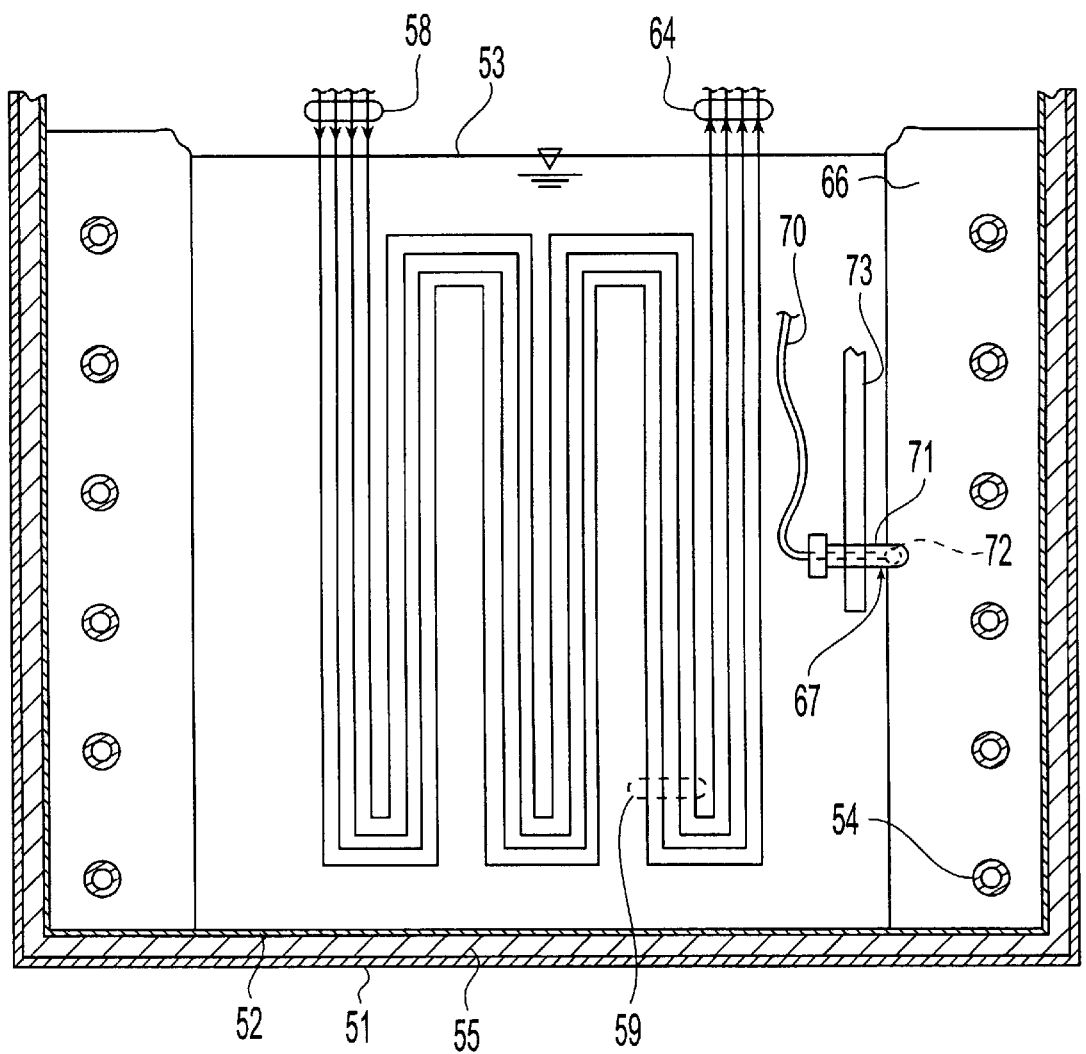

FIGS. 7 & 8 are cross sections of a beverage chiller which will be used to describe an embodiment of the present invention and its operation in more detail. The beverage cooling coils, which in this embodiment are syrup cooling coils 59, and syrup conveying and delivery tubing 58, 64, respectively, are depicted schematically for clarity. The syrup coils 59 are commonly bundled together and arranged in a plurality of "U-shaped" pendants as shown; however, there are other suitable arrangements possible for the coils 59 as will be readily apparent to those skilled in the art. This syrup coil 59 arrangement maximizes the coil surface area in contact with the ice cold water bath 53, thereby concomitantly maximizing the heat transfer rate. Although the bundles of syrup cooling coils 59 are shown with a vertical orientation, they may be oriented in any suitable direction.

The water bath cooling coils 54, which are preferably tubular in shape, are represented in FIGS. 7 & 8 by circles depicting cross-sections of the tubular coils. Preferably, several vertical levels of horizontal water bath cooling coils 54 may be provided to ensure that a substantially uniform ice bank 66 forms around the inside perimeter of the water tank 52. It should be recognized that the cooling coils 54 need not be configured horizontally, but may also be arranged vertically, diagonally, or in any combination thereof that is suitable. Moreover, it should be noted that the cold element need not be configured as coils with open spaces therebetween, but may be any suitably shaped element or combination of elements which is capable of being sufficiently cooled by a refrigerant coolant to form an ice bank. For example, substantially hollow and parallel plates, solid thin plates with integral hollow passageways to accommodate the flow of a refrigerant, coils wherein the open spaces therebetween are filled by a thin solid sheet membrane, finned coils, etc. may be used; the configuration being a matter of design choice.

The temperature probe sensor 67 used in this ice bank embodiment is essentially similar to that described before in reference to FIG. 2, having a preferably thin-walled housing 71 which is substantially hollow, and preferably a thermistor bead 72 with wire leads encapsulated therein. The housing 71, however, need not necessarily be made of food-grade material because it does not contact a liquid intended for human consumption, unlike the ice-making machine described above. The consumable syrup and carbonated water remain completely contained inside their respective tubing and/or coils, and are thus isolated from the water bath 53. The thermistor bead 72 is preferably in contact with the housing 71 so that essentially the same temperature is sensed by the bead as exists on the exterior of the housing. It should be recognized that other types of sensors (i.e., thermocouples, resistance temperature detectors ("RTDs"), etc.) may also be used.

Preferably, the thermistor bead 72 is self-heated (by the resistive effect of electric current flowing in the thermistor as described above) to prevent ice from forming near the bead on the probe housing 71 which is immersed in the cold water bath 53. This minimizes the chance of ice forming near the sensor 67, which would generate a false indication that the ice bank 66 has formed to a sufficient degree to reach the sensor 67. It should be noted, however, that the thermistor bead 72 need not be self-heated.

The temperature sensor 67 is mounted in a carrier 73 which may be made of plastic, metal, or any other material suitable for the intended application. The carrier 73 allows the sensor 67 to be positioned and located at a point in the water tank 52 where it is desired to allow the growth of the ice bank 66 to reach. Accordingly, the sensor 67 limits the growth of the ice bank 66.

The carrier 73 may be mounted to the housing 51 of the chiller 50 or to any convenient internal support members contained therein. The carrier 73 may further comprise an adjustable mount to allow sensor 67 to be positioned closer or farther from the ice bank 66 to meet the requirements of the particular intended application. In general, this may be accomplished by either (1) making the entire carrier's 73 position adjustable in relation to the ice bank (with the position of sensor 67 being fixed in relation to the carrier), or (2) by making the sensor 67 slidable in and out from the plane of the carrier as shown in FIG. 7 (with the position of the carrier being fixed in relation to the chiller housing 51). The detailed design of the carrier 73, including its configuration, are well within the knowledge of those skilled in the art and is a matter of design choice. Accordingly, numerous configurations are possible consistent with the teachings herein.

Control and temperature sensing circuitry are also provided which are associated with the temperature probe sensor. The circuitry may implement control logic which is configured to control the operation of the beverage chiller.

With reference to FIG. 7, the temperature probe sensor 67 operates as follows. As refrigerant circulates through the water bath cooling coils 54, an ice bank 66 forms around the coils 54 which keeps the water bath extremely cold. At this juncture, the ice bank 66 is separated from the sensor 67 by a distance "D" as shown. Accordingly, the temperature sensor 67 will sense the temperature of the cold water (liquid phase) which will generally be above freezing (i.e., 32 degrees Fahrenheit).

The thickness of the ice bank 66 will progressively continue to grow outwards from the cooling coils 54 towards the center of the water bath 53 and temperature sensor 67 (see directional arrows). As the ice bank gets closer to the temperature probe sensor 67, the sensed temperature continues to get progressively colder. Eventually, the ice bank will reach and contact the temperature probe sensor 67 as shown in FIG. 8, whereby a very low temperature (e.g., 32 degrees Fahrenheit or less) will be sensed by the sensor and temperature sensing circuitry. This event triggers the circuitry to turn off the refrigerant compressor 56 (FIG. 6) as described in more detail as follows.

It should be noted that to perform the control functions mentioned above, the control logic may comprise signal-sensing circuitry, a temperature signal threshold value, threshold persistence circuitry, and compressor control (e.g., on/off) circuitry. The signal-sensing circuitry senses the signal from the temperature probe sensor 67 which represents the temperature sensed by the sensor 67. The temperature signal threshold value is predetermined and preprogrammed into the control logic to establish the temperature at which it is desired to turn off the compressor. The temperature signal threshold value is selected to represent a temperature at which the ice bank contacts the temperature probe sensor 67. The persistence circuitry ensures that the temperature signal has consistently remained above the threshold value for a preprogrammed time duration after the temperature signal first exceeded the threshold value. The persistence circuitry helps avoid false sensed temperatures that do not actually reach the threshold value.

Figure 9:
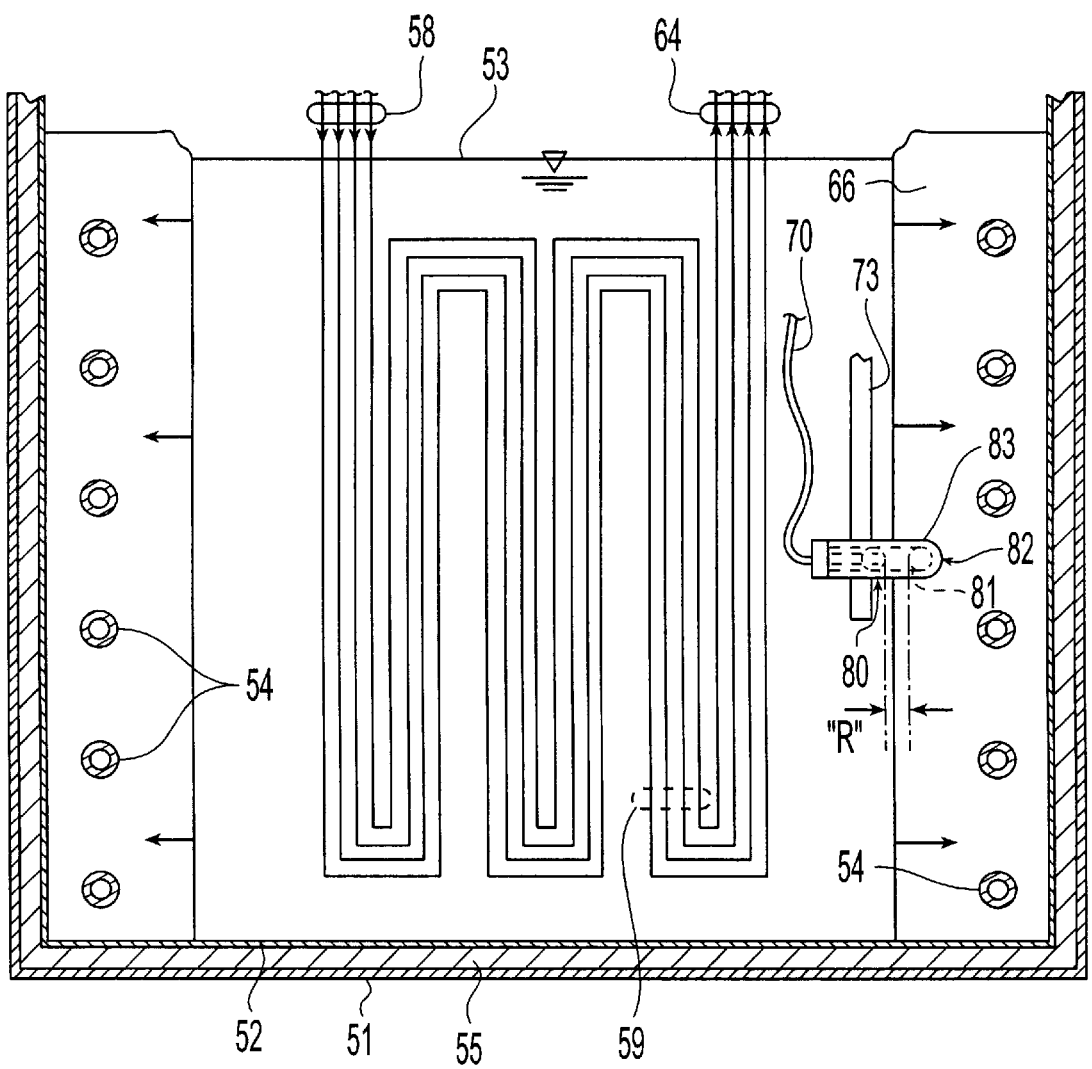
FIG. 9 is a schematic cross-sectional side view of a beverage chiller of the present invention including a two temperature sensors in a single housing and temperature-detection circuitry.

Gradually over time after the circuitry has shut off the compressor 56, the ice bank 66 will slowly begin to recede and shrink away from the probe back towards the water bath cooling coils 54 (see, e.g., FIG. 9 directional arrows). Concomitantly, the temperature of the water batch will gradually begin to increase as well which means that the syrup temperature also will increase. The refrigerant compressor must be restarted which can be accomplished in many ways. In one embodiment, an elapsed time counter is started at the same time that the compressor 56 is shut off by the control circuitry as described above. After a predetermined amount of time $T_{elapse}$ has elapsed, the compressor control circuitry automatically restarts the compressor 56. The amount of elapsed time $T_{elapse}$ after which the compressor 56 will be restarted may be determined empirically and preprogrammed into the control logic.

The refrigerant compressor 56 may also be restarted based on sensing various temperatures associated with the operation of the beverage chiller. For example, in one embodiment the temperature of the water bath may be monitored and a water bath threshold value may be preprogrammed into the control logic. When the bath threshold temperature is exceeded, the compressor will be started. The water bath temperature may be sensed by providing a separate temperature sensor for that purpose, or by using the same temperature probe sensor 67 (described above) which is also used to turn off the compressor 56. In this latter case, the temperature sensor 67 serves multiple functions, and the control logic may be configured to allow this single sensor to be used to turn the compressor off, monitor the water bath temperature, and then turn the compressor on again as needed.

In another embodiment shown in FIG. 9, a temperature probe sensor 82 is provided which contains two thermistor beads 80, 81 spaced apart by a predetermined axial distance "R" within the probe housing 83. Thermistor 80 is used to sense a "compressor off" temperature signal threshold value which is preprogrammed into the control logic and which will be met or exceeded when the ice bank 66 grows and reaches the temperature probe sensor housing 83 adjacent to the thermistor. At that juncture, the probe housing 83 adjacent to the other thermistor 81 will also be in contact with the ice bank 66. Accordingly, thermistor 81 will sense substantially the same temperature (i.e., the "compressor off" threshold temperature) as thermistor 80.

After the compressor is turned off by the circuitry, the ice bank 66 will begin to slowly melt and recede towards the water bath cooling coils 54 (see FIG. 9 directional arrows). Thermistor 81 will continue to sense the "compressor off" threshold temperature as long as the ice bank remains in contact with the probe housing 83 adjacent to thermistor 81 as shown in FIG. 9. When the ice bank 66 eventually recedes far enough so that the bank is no longer in contact with the housing 83 adjacent to thermistor 81, a water bath 53 temperature warmer than the "compressor off" threshold temperature will be sensed by thermistor 81. At some point in time the water bath 53 temperature will meet or exceed a predetermined "compressor on" temperature signal threshold value which has been preprogrammed into the control logic. The circuitry will then start the compressor in order to cause the ice bank 66 to begin to grow again. The foregoing cycle of ice bank growth and melting will then be repeated, with the result that the front of the ice bank will be maintained within, or close to, the region "R" defined between the two thermistors.

Figure 10:
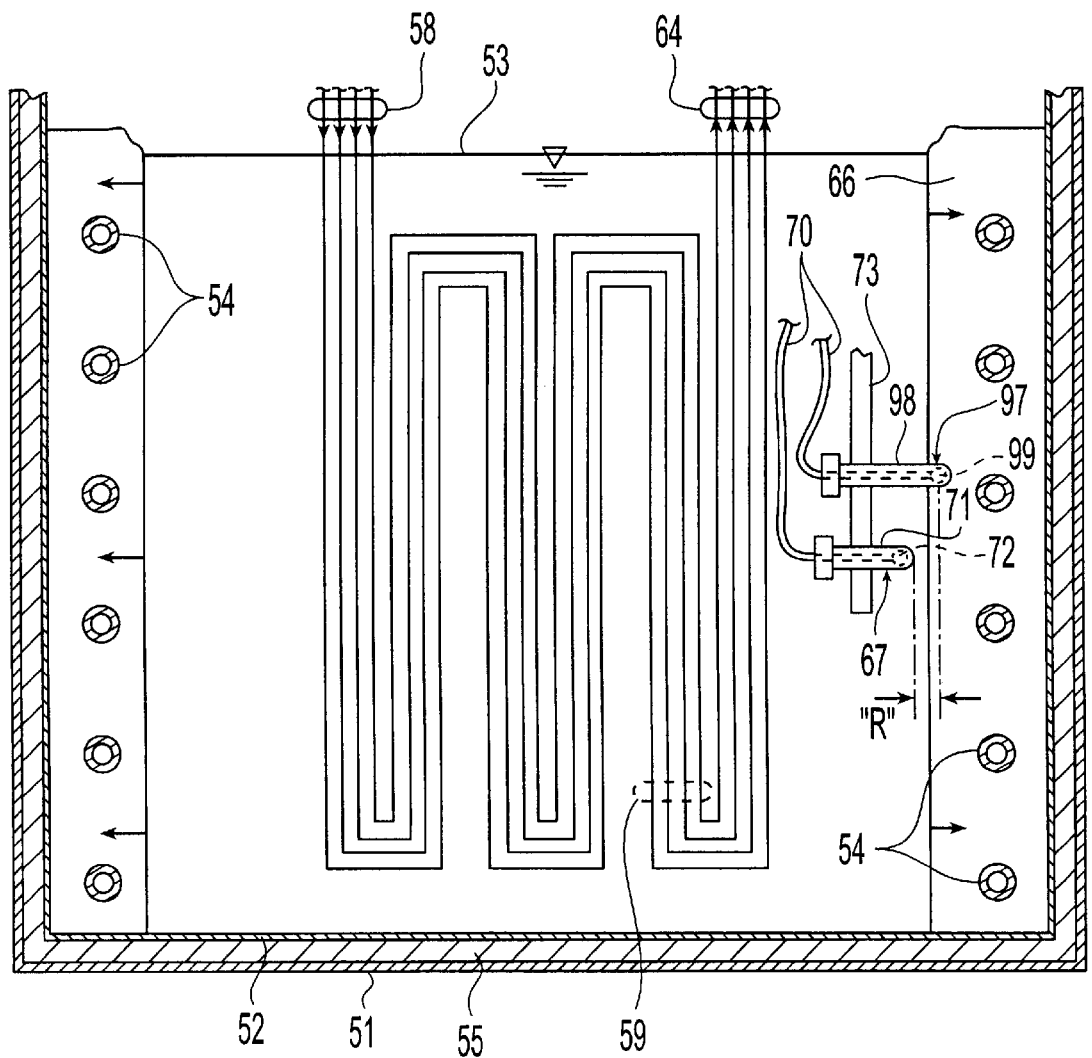
FIG. 10 is a schematic cross-sectional side view of a beverage chiller of the present invention including two temperature sensors in separate housings and temperature-detection circuitry.

FIG. 10 shows another embodiment having a second temperature sensor to restart the compressor under the same operating scenario described for FIG. 9 above. In this case, however, a second temperature probe sensor 97 is provided having its own separate probe housing 98 and thermistor bead 99 similar to sensor 67. The temperature sensor 97 is positioned and located to create an axial distance "R" between sensors 97 and 67. Although axial distance "R" is achieved in the embodiment shown by making probe housing 98 longer than probe housing 71, and using the same carrier 73 to hold both temperature sensors 67 and 97, the invention is not limited to this arrangement. For example, a separate carrier may be used for mounting and holding second sensor 97 wherein both sensors 67 and 97 have the same probe housing length (not shown). Accordingly, numerous suitable arrangements of probe carriers and temperature sensor probes are possible which are a matter of design choice.

The temperature sensor(s) and circuitry of the present invention as applied to ice bank applications are not limited to the embodiments described herein. Accordingly, numerous variations are possible without departing from the spirit of the invention which will be readily recognized by those skilled in the art. For example, two or more probes containing a single thermistor as shown in FIGS. 7 & 8 may be used and placed at physical different locations in the beverage chiller to ensure that a uniform ice bank is being formed. More than one double thermistor probe as shown in FIG. 9 may also be used and placed at different physical locations in the beverage chiller as well.

It will further be appreciated that the sensor(s) and circuitry of the present invention may be used in many ice bank machine applications employing a chiller where it is desired to cool beverages for subsequent dispensing through a beverage dispenser (e.g., non-carbonated beverages, beer, wine, juice, etc.). Furthermore, the invention is more broadly applicable to any machine employing the use of an ice bank and is expressly not limited to beverage chiller applications alone.

What is claimed is:

1. A machine for forming an ice bank comprising:
   a tank having water disposed therein;
   a cold element including at least one ice-forming surface cooled to below the freezing point of the water, at least part of the cold element being submerged in the water such that a bank of ice forms around the surface;
   at least one temperature sensor inside the tank; and
   circuitry associated with the sensor for detecting when the bank of ice reaches the sensor, the circuitry being operative to sense a temperature signal from the sensor, wherein the at least one temperature sensor is sufficiently self-heated to prevent ice from forming on the sensor.

2. The ice bank-forming machine of claim 1 wherein the at least one temperature sensor is provided with sufficient current for self-heating.

3. The ice bank-forming machine of claim 1 wherein the cold element is comprised of refrigerant-cooled coils configured to form an ice bank.

4. The ice bank-forming machine of claim 1 wherein the temperature sensor is a thermistor-type sensor.

5. The ice bank-forming machine of claim 4 wherein the thermistor-type sensor comprises a bead in a metal housing.

6. The ice bank-forming machine of claim 4 wherein the temperature sensor is sufficiently self-heated to prevent ice from forming on the sensor.

7. The ice bank-forming machine of claim 1 wherein a second temperature sensor is provided, the circuitry being further operative to sense a temperature signal from the second sensor, the two temperature sensors being spaced apart axially by a predetermined distance along the direction of the growth of the ice bank.

8. The ice bank-forming machine of claim 7 further comprising a single probe housing containing the two sensors.

9. The ice bank-forming machine of claim 7 wherein both temperature sensors are sufficiently self-heated to prevent ice from forming on the sensors.

10. The ice bank-forming machine of claim 1 wherein the machine is a beverage chiller.

11. The ice bank-forming machine of claim 1 wherein the circuitry controls the thickness of the ice bank forming on the surfaces of the cold element.

12. A beverage chiller comprising:
    an exterior casing;
    a tank containing water disposed in the casing;
    a refrigerant compressor associated with beverage chiller;
    a plurality of coils at least partially submerged in the water and connected to the compressor to form a closed flow circulation loop, the compressor and coils containing a refrigerant coolant whereby the coils are cooled to below the freezing point of water to form an ice bank;
    a sensor disposed inside the tank for sensing temperature, the sensor being sufficiently self-heated to prevent ice from forming on the sensor;
    circuitry associated with the sensor for detecting when the ice bank reaches the sensor, the circuitry being operative to sense a temperature signal from the sensor, wherein the circuitry controls the growth of the ice bank.

13. The beverage chiller of claim 12 wherein the sensor is a thermistor-type sensor comprising a bead in a metal probe housing.

14. The beverage chiller of claim 12 wherein the circuitry is operative to turn off the compressor when the ice bank reaches the sensor.

15. The beverage chiller of claim 12 further comprising a second sensor, the circuitry is operative to further sense a second temperature signal from the second sensor, the two temperature sensors being spaced apart axially by a predetermined distance along the direction of the growth of the ice bank.

16. The beverage chiller of claim 15 wherein the circuitry is operative to turn on the compressor when the ice bank recedes from the second sensor.

17. The beverage chiller of claim 15 wherein both sensors are disposed in a single probe housing.

18. The beverage chiller of claim 12 further comprising a plurality of beverage cooling coils at least partially submerged in the water.

19. A method of operating a machine for forming an ice bank comprising the steps of:
    a. providing a tank having water disposed therein;
    b. providing a cold element including at least one ice-forming surface, at least part of the cold element being submerged in the water such that an ice bank can form and grow around the surface;

c. providing at least a first temperature sensor, the sensor being a thermistor-type sensor that is sufficiently self-heated to prevent the formation of ice on the sensor;

d. providing circuitry associated with the sensor for detecting when ice reaches the sensor, the circuitry being operative to sense a temperature from the at least first sensor;

e. cooling the cold element to below the freezing point of water;

f. forming and growing an ice bank around the ice-forming surfaces;

g. sensing a temperature signal from the sensor;

h. determining when the temperature signal reaches a predetermined threshold value; and i. controlling the operation of the machine to control the growth of the ice bank.

20. A method of operating a machine for forming an ice bank comprising the steps of:

a. providing a tank having water disposed therein;

b. providing a cold element including at least one ice-forming surface, at least part of the cold element being submerged in the water such that an ice bank can form and grow around the surface;

c. providing at least a first temperature sensor, the sensor being a thermistor-type sensor that is sufficiently self-heated to prevent the formation of ice on the sensor;

d. providing sufficient current to the sensor to cause the self-heating;

e. providing circuitry associated with the sensor for detecting when ice reaches the sensor, the circuitry being operative to sense a temperature from the at least first sensor;

f. cooling the cold element to below the freezing point of water;

g. forming and growing an ice bank around the ice-forming surfaces;

h. sensing a temperature signal from the sensor;

i. determining when the temperature signal reaches a predetermined threshold value; and j. controlling the operation of the machine to control the growth of the ice bank.

21. The method of claim 19 wherein controlling the operation of the machine further comprises turning the machine off to stop the growth of the ice bank when the temperature threshold value is reached.

22. The method of claim 21 further comprising the step of providing the circuitry with a predetermined time delay and wherein controlling the operation of the machine further comprises turning the machine back on to restart the growth of the ice bank when the time delay has been met.

23. The method of claim 21 further comprising the step of providing a second temperature sensor, the circuitry being operative to sense a temperature signal from the second sensor, and determining when the temperature signal from the second sensor reaches a predetermined second threshold value.

24. The method of claim 23 wherein controlling the operation of the machine further comprises turning the machine on to restart the growth of the ice bank when the temperature signal from the second sensor reaches the predetermined second threshold value.

* * * * *